United States Patent [19]

Lombardo et al.

[11] Patent Number: 4,959,211

[45] Date of Patent: Sep. 25, 1990

[54] PROCESS FOR THE PRODUCTION ON AN ANTIVIRAL VACCINE, PARTICULARLY ANTI-FOOT AND MOUTH DISEASE VACCINE

[76] Inventors: Jorge H. Lombardo, Itvzaingo 865, 1244 Moreno; Eduardo E. Smolko, Rioja 2897, (1636) Olivos, Buenos Aires; Rodolfo A. Ugalde, Chile 740, Haedo Buenos Aires 1706; Scholein Rivenson, Vidt 2027, 4th-10-Buenos Aires, all of Argentina

[21] Appl. No.: 184,784

[22] Filed: Apr. 22, 1988

[30] Foreign Application Priority Data

Apr. 28, 1987 [AR] Argentina ............................. 307406

[51] Int. Cl.$^5$ ............................................ A01N 63/00
[52] U.S. Cl. ........................................ 424/93; 424/90
[58] Field of Search ............................. 424/90, 89, 93

[56] References Cited

PUBLICATIONS

Baldelli et all, "Gamma Radiation for Sterilizing the Carcasses of Foot-and-Mouth Disease Virus Infected Mammals," Int'l Atomic Agency Report, pp. 77-86 (1967).

Primary Examiner—John F. Niebling
Assistant Examiner—Isabelle Rodríguez
Attorney, Agent, or Firm—Wells & White

[57] ABSTRACT

The instant invention relates to a process in which important improvements are introduced in virus production and inactivation steps, as well as in the vaccine formulation step. The virus is reproduced in animals immuno-depressed through ionizing radiations, thus making it possible to use adult host animals, not naturally sensitive to the virus, with the advantage of using all types of tissues thereof. Bacterial infections are prevented by antibiotic administration. Virus inactivation is also obtained through ionizing radiations. Radiation doses do not affect antigenic properties, as may be noted from the interpretation of the Target Theory.

17 Claims, 4 Drawing Sheets

PROCESS FOR THE PRODUCTION ON AN ANTIVIRAL VACCINE, PARTICULARLY ANTI-FOOT AND MOUTH DISEASE VACCINE

BACKGROUND OF THE INVENTION—PRIOR ART

The instant invention relates to a novel process for preparing antiviral vaccines, particularly anti-foot and mouth disease vaccine.

As already known, the different processes for preparing vaccines against viral diseases are comprised by a sequence of steps which, although different in accordance with particular viruses and processes selected, may be classified as follows:
1. one or more steps for virus production;
2. one or more steps for virus inactivation; and
3. one or more steps for vaccine formulation.

The object of the present process invention has novel basic features in virus production and inactivation steps, and also proposes other novel steps and complementary stages through the whole process as preferred alternatives.

In accordance with the present invention, virus production is higher than that obtained through other known processes basically due to the fact that animals used are previously radiated with an ionizing radiation dose determined experimentally.

On the other hand, virus inactivation also is improved as compared to that obtained through techniques of known processes, due to the fact that ionizing radiations are also used, which were experimentally determined. The reason why better results are obtained is that radiation is carried out over a viral suspension at a very low temperature ($-40°$ C. or lower), thus avoiding virus degradation through the action of enzymes present in the viral culture medium.

Foot and mouth disease virus easily reproduces in mice, rats, hamsters and rabbits not more than 8 days old. Sensitivity to virus decreases as the age of the animals increases; thus, in adult animals, even high viral doses do not produce noticeable alterations.

However, it is important to use organs of adult animals for viral production in order to diminish production costs.

In accordance with the process of the instant invention virus production is carried out in an animal previously subjected to immunodepression through ionizing radiations, thus becoming sensitive to foot and mouth disease virus even when adult, and in tissues which are normally not sensitive to the virus.

In prior art anti-foot and mouth disease vaccines virus production was carried out by infecting bovine cattle, which are particularly sensitive to the virus, and then removing the viral material present in the tongue epithelium.

The material thus obtained, besides being scarce, was subjected to frequent contamination; therefore, vaccine mass production was practically unfeasible due to the cost and operating difficulties.

Further, survival culture of bovine tongue epithelium obtained from animals killed in slaughterhouses as support for viral reproduction was introduced (Frankel method). This method is still now one of the most widely used in the industry for the reproduction of foot and mouth disease virus for preparing vaccines.

Nevertheless, bacterial contamination of survival cultures is frequent, the collection of epithelia under proper conditions is difficult and frequent errors take place when obtaining antigens due to epithelia contamination or degradation. Therefore, costs per unit vaccine are high.

More recently, BHK (Baby Hamster Kidney, line 21, clon 13) cell culture was introduced; cell cultures in suspension are used for virus reproduction.

Such a process requires the use of sophisticated devices in order to maintain cell multiplication (Synthetic or semi-synthetic means with the addition of fetal sera). Due to their high cost, fetal sera have been replaced by adult bovine serum, but the use of the latter causes the risk of neutralizing antibodies which, in many cases, completely prevents virus reproduction. Further, cell adaptation to suspension culture is required, as well as virus adaptation to its multiplication in these cell cultures, with corresponding risks of antigen modification. Lastly, expensive equipment is required in order to guarantee culture bacterial sterility.

The process of the instant invention, in the steps corresponding to the obtaining virus, is improved over the processes of the prior art, basically due to the fact that it transforms the whole animal into a medium appropriate for virus reproduction, this fact being valid also for adult rodents and ruminants.

In fact, prior to virus inoculation, the animal is completely irradiated with ionizing radiation in a dosage that is between a minimum value for assuring immunological depression and a maximum value for assuring animal survival until its death caused by the action of the highly proliferated virus. Optimum dosages were found to be between 700 and 2700 rads (according to the species).

It was also found that a period of time of 24–36 hours between irradiation and virus inoculation was convenient in order to obtain the best results.

Another important improvement is the use of antibiotics during the viral proliferation period, in order to avoid bacterial reproduction promoted by the immunodepression caused by radiations.

In this way, an economical, technologically simple, high quality viral antigen source is obtained, which also bears a low contamination risk and low antigen modification rates.

Since known methods of virus collection may be applied to some tissues or cultures, the following collection step is preferred.

This step comprises removing skin and viscerae from the host animal. Soft parts are removed from the rest of the cadaver and are crushed with the addition of saline solution; the mixture obtained should be visually homogeneous.

Lastly, a liquid phase is separated by means of filtration or centrifugation, thus obtaining the required active viral suspension.

In relation to virus inactivation, the known methods are based on the chemical action of some substances, such as acethylethylenimine, betapropiolactone, glycidaldehyde, ethylethylenimine, bis-ethylenimine (BEI) or formaldehyde. In such a process, the viral suspension should be kept at room temperature or higher temperatures for 24–48 hours.

Under these conditions, physical and chemical agents act to degrade the virus antigenic proteins.

On the contrary, radiation with ionizing radiations, in the mentioned dosages, carried out at extremely low temperatures (typically −70° C., and always below 0° C.) does not cause the mentioned enzymic reactions.

Virus radiation with ionizing rays is already known in the art, but not for the purpose of the instant invention, but for forming part of the basic investigations.

Ernest Pollard, U.S., has applied radiation for obtaining inactivation of some virus properties (Inactivation Theory).

Another known reference of prior art is that disclosed by William Ginoza, "Inactivation of viruses by ionizating radiations and by heat", Methods in Virology, IV, pages 139–205 (1968).

Nevertheless, none of the above references are related to the use of radiations for obtaining industrial production of vaccine.

Ionizing radiation used for radiating animals as well as for inactivating the viruses may be of the electromagnetic radiation type, such as X-ray or Gamma-ray, or of the particle radiation type, such as alpha-particles, positions, electrons, protons, neutrons or deuterons.

Whichever its origin, foot and mouth disease antigen has a rather poor immunological ability. Therefore the antigen should be improved by other substances capable of exerting immunity coadjutant action, in relation to power as well as to duration.

In accordance with known processes, aqueous or oily carriers may be used. The former include aluminum hydroxide and the duration of the immunity obtained is not longer than four months. The second are emulsions, but in this case known vaccines have relatively large droplets, and in some cases their stability is low, thus causing rupture of the emulsion.

With the process of the present invention it is possible to obtain a minimum immunity term of six months, thus reducing the vaccine administration to bovines to twice a year.

Therefore, the instant invention proposes a formulation comprising producing a "water in oil" type emulsion, the discontinous internal phase of which is constituted by the inactivated viral suspension and its external dispersion phase comprises a mineral oil.

The mineral oil, acting as immunity adjuvant, is of the liquid paraffin type, which is a mixture of different proportions of paraffins and naphtenes, but lacking cyclic hydrocarbons due to their probable carcenogenic action.

Another suitable oil is polybutene, which is an oily hydrocarbon prepared through polymerization of olefins, mainly comprised by methylated isobutenes of constant formula.

Whichever the selected oil may be, when the antigen is to be concentrated or the emulsion viscosity is to be lowered, the viral suspension is previously adsorbed to the aluminum hydroxide with 2% aluminum oxide.

In both cases, and in order to obtain a low viscosity, stable, homogeneous emulsion of the type "water in oil", having small droplets (of a diameter not larger than 0.1 micron) and easy to be obtained at an industrial scale, three emulgents are employed: a lipophilic emulgent, sorbitan sesquioleate of hydrophilic-lipophilic balance (HLB) 3.7; a hydrophilic emulgent, polyoxiethylene sorbitan mono-oleate, HLB 15, in the case of an oil emulsion of the viral solution, or HLB 10 when the viral suspension is incorporated to aluminum hydroxide; and n-butanol as co-surfactant.

The object is to obtain any of the following formulations:

| | |
|---|---|
| 1. Liquid paraffin | 40.50% |
| Sorbitan sesquioleate | 6.50 |
| Polyoxiethylene sorbitan mono-oleate, HLB 15: | 1.00 |
| n-butanol | 2.00 |
| Inactive viral suspension | 50.00 |
| 2. Polybutene | 40.50 |
| Sorbitan sesquioleate | 6.50 |
| Polyoxiethylene sorbitan mono-oleate, HLB 15 | 1.00 |
| n-butanol | 2.00 |
| Inactive viral suspension | 50.00 |
| 3. Liquid paraffin | 53.60–43.60 |
| Sorbitan sesquioleate | 2.00 |
| Polyoxiethylene sorbitan mono-oleate, HLB 10 | 2.40 |
| n-butanol | 2.00 |
| Aluminum hydroxide plus inactive viral suspension | 40.00–50.00 |
| 4. Polybutene | 53.60–43.60 |
| Sorbitan sesquioleate | 2.00 |
| Polyoxiethylene sorbitan mono-oleate, HLB 10 | 2.40 |
| n-butanol | 2.00 |
| Aluminum hydroxide plus inactive viral suspension | 40.00–50.00 |

The steps involved in the process are the following:

(a) Mineral oil and emulgents are mixed into a tank at 4° C.;

(b) viral suspension, pure for formulations 1 or 2, or mixed with aluminum hydroxide in the case of formulations 3 or 4 (stirring for two hours, 1 part aluminum hydroxide and 1–5 parts of viral suspension, in accordance with the concentration desired) is introduced into another tank at 4° C., settling is allowed for 24 hours, and supernatant needed for returning to the original volume of aluminum hydroxide is removed;

(c) contents of both tanks are poured into a closed and sterile loop homogenizator, operating under high pressure and continuous flow;

(d) the product is collected into a third tank.

SUMMARY OF THE INVENTION

In general, the above process for producing anti-foot and mouth disease vaccine may be used for the production of other antiviral vaccines, provided some modifications are made, which do not affect the general scope of the invention.

Therefore, an object of the instant invention is to provide a process for preparing antiviral vaccines on an industrial scale with minimum risks caused by contamination, bacterial proliferation or virus degradation through physical or chemical action.

Another object of the invention is to provide a process for preparing a low cost antiviral vaccine.

Still another object of the invention is to provide a process for preparing an antiviral vaccine suitable for different types of viruses, such as that producing foot and mouth disease.

A further object of the invention is to provide a process for preparing an antiviral vaccine, particularly an anti-foot and mouth disease vaccine, wherein virus production is effected on adult animals, even those animals which are not naturally sensitive to the virus, such as hamsters, in almost all their organs and tissues.

Another object of the invention is to provide a process for preparing a vaccine wherein, once the active viral suspension is obtained, the same is inactivated by a method withstanding low temperatures and assuring its antigenic character.

Finally, another object of the invention is to provide a process for preparing an anti-foot and mouth disease vaccine which provides a longer immunity period.

BRIEF DESCRIPTION OF THE DRAWINGS

Table 1 lists viral proliferation results on previously radiated animals.

DETAILED DESCRIPTION OF THE INVENTION

Viruses irradiated with ionizing radiations may be fully destroyed by high doses, while, under controlled conditions, partial inactivation of different viral properties, such as hemoagglutination, antigenicity, uneffectiveness, etc. may be obtained.

The loss of infective ability of the virus thus obtained permits the production of suitable materials for vaccine preparation.

The conditions under which such material is obtained are established through the study of virus inactivation curves, which allow determination of the minimum dose to be applied for obtaining non-infective materials, and which are obtained plotting the number of units surviving radiation vs. dosage. The curve thus obtained is known as Survival Curve or Dose-Response curve and differ from other survival curves in that the latter may not be explained only in biological variability terms.

The above gave rise to the interpretation of the results through the so-called "Impact Theory", also known a Target Theory, which widely explains different kinds of survival curves.

Considering the results obtained through investigation and experiments, inactivation curves not only depend on virus external factors, such as dosages, radiation rates, radiation type, temperature and nature of the substrate on which virus is hosted during the process, but also on the characteristics of the virus per se, such as its chemical composition, e.g. DNA or RNA nucleus, or on the nature of its molecular structure such as, for example, one or more single or double conjugated chains.

FIG. 1 shows the results obtained in the following cases:

(a) inactivation of Rauscher Murine Leukemia virus;
(b) inactivation of Herpes Simplex virus,
(c) inactivation of foot and mouth disease virus.

In all cases, the intersection of the curve with the X-axis gives the dose needed for inactivating $10^6$ times the original population, i.e. In/Fn=1.000.000 wherein In stands for Initial number and Fn for Final number of viral particles after the process.

For foot and mouth disease virus, inactivation of the three types thereof existing in Argentina (A. O. C) was carried out through gamma-radiation, results similar to those shown on the graph being obtained.

In all cases, foot and mouth disease virus inactivated by ionizing radiation fully retains its ability for fixing to the complement in the presence of anti-foot and mouth disease hyperimmune serum.

With the viruses reproduced in irradiated animals, being the viruses inactivated by ionizing radiation, monovalent and trivalent experimental anti-foot and mouth disease vaccines were prepared and tested for their power and compared to known vaccines. Similar or better results were obtained.

Curve -a- in FIG. 1 represents the inactivation of Rauscher Murine Leukemia virus of which comprises two RNA complexed chains designed as R-MuLV and R-SFFV, radiated with gamma-rays.

Curves -b1- and -b2- represent inactivation of viral particles from the Herpes Simplex family designed HSV-1 (Thea) and HSV-2 (Müller), both having DNA, radiated with gamma rays.

Curves -c1- and -c2- represent foot and mouth disease virus A (FMDV) inactivation, subjected to two types of radiation, namely gamma radiation from Co 60 and accelerated particles radiation (27 MeV deuterons) from Syncrocyclotron at, Buenos Aires, respectively.

FIG. 2 shows the plan of the room in which ovine and bovine cattle was irradiated with Co 60.

The equipment is a "Gamma beam 150" from the Radiobiology Center of the Agronomy and Veterinary Faculty, Buenos Aires University.

Reference numeral 1 designates cobalt source 60. The animal was located in a wooden container 2; free spaces were filled with a material similar to tissue to assure an even radiation.

The animal received a half-dose while its mean longitudinal line remained following a 1.10 m radius circumference. The other half-dose was received placing the animal in an inverted position, i.e. with the other side towards source 1.

Numeral 3 represents the access door and number 4 the command room.

Due to the importance of dosimetry for the correct result evaluation, checking of the dose was considered necessary. This was carried out with a thermo-luminiscent dosemeter introduced into the animal through oral or rectal route. This process gives a correct idea of the dose introduced into the animal.

Table I shows the results obtained by virus inoculation in adult rodents and previously radiated bovines.

When carrying out the process of the invention, those skilled in the art may introduce modifications and/or improvements, all of which are to be considered within the scope of the instant invention which is only determined by the spirit and scope of the appended claims.

TABLE I

| SPECIES USED AGE (weeks) | | DOSE (rad) | CONTROL METHODS: Titration for organ mixture: minimum (10 exponent) | maximum | C.F. |
|---|---|---|---|---|---|
| Hamsters (*Cricetus acureatus*) | | | | | |
| 8–11 | R + V | 800 | 7.1 | 9.4 | ++++ |
| | R + V + A | 800 | 7.9 | 10.4 | ++++ |
| | R + V + A (virus passages) | 800 | 10.4 | 12.5 | ++++ |
| Pirbright Mice | | | | | |
| 3–4 | R + V | 600 | 5.5 | 6.5 | ++++ |
| | R + V | 800 | 5.5 | 7 | ++++ |
| 7–8 | R + V | 600 | 3.4 | 4.2 | ++++ |
| | R + V | 800 | 4.7 | 5.4 | |
| C3H/Ep. Mice | | | | | |
| 7–8 | R + V | 700 | 3.5 | 4.5 | ++++ |

TABLE I-continued

| | | CONTROL METHODS | | |
| --- | --- | --- | --- | --- |
| | | Titration for organ mixture | | |
| SPECIES USED AGE (weeks) | DOSE (rad) | minimum (10 exponent) | maximum (10 exponent) | C.F. |
| | 900 | 5.4 | 6.4 | ++++ |
| Wistar rats | | | | |
| 7-8  R + V | 1,200 | 4.5 | 7.5 | ++++ |
| Ovines | | | | |
| 24-50  R + V + A | 2,700 | 4.8 | 6.5 | ++++ |
| Affected muscle (mass proliferation of virus) | | | | |
| R + V + A | 2,700 | 6.3 | 8.4 | ++++ |
| Ovines inoculated with virus serial groups | | | | |
| R + V + A | 2,700 | 7.8 | 8.6 | ++++ |

Notes:
R: radiation
V: virus.
A: antibiotic
F.C.: complement fixation

The following is a plan for producing 1,000,000 doses monthly of trivalent anti-foot and mouth disease vaccine (eventually tetravalent vaccine).

(1) Hamsters (Cricetus aureatus, 60–70 days old, male and female, in the required amount (480 per month).

(2) The required amount (approximately 120 hamsters) are transferred to the room in which radiation takes place and are subjected to a radiation dose comprised between 700 and 1200 rads.

(3) During the time comprised between 24 hours before radiation and the time in which virus is inoculated, which is 24 to 36 hours after, radiation antibiotics are injected in to the animals (Gentamicine, 4 mg/kg daily, in a single dose or divided into two doses).

(4) Animals are located in a laboratory room specially designed for this end and into containers assuring asepsis, and fed with sterile food and water.

(5) 24–36 hours after radiation, active virus is inoculated. Virus is contained in bovine origin material, in the form of i.m. injectable suspension.

(6) Animals are permanently checked in order to determine their death, upon which cadavers are collected and viscerae and skin are removed therefrom, and are kept into freezers at −40° C.

(7) Material gathered (sufficient for 1,000,000 monovalent doses) with the addition of saline solution, is crushed until a homogeneous suspension is obtained, separated by filtration and centrifugation. (Prior to the last centrifugating operation, chloroform is added up to a maximum of 5%).

(8) After a final filtration, the active viral solution is again frozen at −40° C. into plastic containers suitable for further inactivation through radiation.

(9) The above material is inactivated by radiation from cobalt beams in suitable containers and is kept frozen through contact with dry ice (−70° C.).

(9′) Samples for titration and classification (types).

(10) Radiation dose for anti-foot and mouth disease vaccine is of 4 Mrads.

(11) Vaccine formulation

Virus is diluted until titration is obtained, one titre of $10^7$ in lactant mice (from an original titration of $10^{10}$ to $10^{12}$ for each viral type).

Hydroxisaponinated vaccine: With the antigen prepared and inactivated by the above technology, hydroxisaponinated vaccine lots are prepared in accordance with classic methods, without virus concentration. Into a sterile tank, at 4° C., 40% of aluminum hydroxide specially prepared to this end with 2% of aluminum oxide is added, then 60% of the viral suspension previously inactivated through radiation is added, containing equal parts of virus, i.e. each 5 ml dose has 1 ml of each antigen for trivalent vaccine. Thimerosal 1:30000 is used as preserver. The mixture is stirred for 2–4 hours, saponine is added (20 ml) of a 5% suspension per liter of vaccine and 50 ml of glycerine per equal volume, as protector.

(12) Oily vaccine:

The formulation of the oily vaccine comprises the following steps:

(a) placing the inactivated viral suspension into a first tank at 4° C.;

(b) mixing a mineral oil of the liquid paraffin type with sorbitan sesquioleate HLB 3.7 as lipophilic emulgent and polyoxiethylene sorbitan mono-oleate HLB 15 as hydrophilic emulgent, into a second tank at 4° C.;

(c) pour the contents of the first and second tanks into a homogenizator;

(d) homogenize, under high pressure, at 4° C., under continuous flow in sterile closed loop, until a stable emulsion is obtained, of the type "water in oil" with homogeneous droplets of no more than 0.1 micron diameter.

(e) collect the emulsion into a third tank, this emulsion comprising the prepared vaccine. Preparation of oily vaccine/aluminum hydroxide.

(a′) place the inactivated viral suspension into a first tank; mix said suspension with aluminum hydroxide, with stirring, for 2 hours, settling during 24 hours. Supernatant is removed in order to obtain the original volume of aluminum hydroxide.

(b′) mix a mineral oil, liquid paraffin or polybutene, with emulgents: polyoxiethylene sorbitan sesquioleate HLB 10 into a second tank.

(c′) proceed as in (c), (d) and (e).

The following steps were carried out for antigen control of viruses reproduced in radiated animals and inactivated through radiations:

(a) monovalent and trivalent experimental anti-foot and mouth disease vaccines were prepared.

(b) these vaccines were tested for their power as compared with known commercial vaccines and the results obtained were the same or better.

Results obtained for anti-foot and mouth disease vaccine allow predicting application of the process of the invention for preparing other antiviral vaccines, in light of the target theory, also called impact theory, of the practical results obtained.

Target theory may be applied to the inactivation of any type of simple bioacting molecule, such as an enzyme or complex micro-organisms such as viruses or bacteria, regardless their size.

Virus inactivation through radiations is based on the assumption of the existence of a sensitive target which is destroyed when one or more impacts fall thereon.

In the case of viruses, this target is well determined and is constituted by viral nucleic acid. Therefore, the viral target analysis also constitutes the analysis of the nuclear structure, and this implies not only the chemical portion but also its molecular framework.

Impact interpretation is differentiated whether the radiation is electromagnetic or corpuscular.

In the first case, the action is directed to a point, absorbed energy producing rupture of a link is the ionizing energy, i.e. E=60 eV.

In the case of corpuscular radiation, rupture is produced basically through the action of a lower energy secondary particle sheath affecting a cross section of the particle path of the beam, which is carried out with a lower energetic yield.

Target theory is based on two physical observations and a postulate:

(1) Ionizing radiations transmit their energy in discrete quantums.

(2) Interactions or impacts are independent from each other and follow Poisson Law.

(3) The response under study takes place if the specific target has received a particular number of impacts.

The target, with a volume v (cubic cm), may represent the sensitive structural size of the radiated object. For mathematical purposes, v is only a parameter measuring sensitivity to radiation.

Dose D may be expressed in terms of impacts per volume unit.

Product $v \times D$ represents the mean number of impacts within the volume v after a dose D, the possibility existing of exactly occurring n impacts due to Poisson distribution:

$$P(n) = (v \cdot D)^n \cdot e^{-v \cdot D}/n!$$

If n impacts are required for producing inactivation of an object, all objects receiving $n-1$ impacts or less will survive.

Survival curve is obtained taking the summatory of all units which received an impact number equal to 0, 1 2, ..., n−1:

$$N/No = e^{-v \cdot D} \sum_{k=0}^{n-1} (v \cdot D)^k/k!$$

wherein N is the survival number and No the population prior radiation.

Theory extension to m targets of the same volume is expressed by the mortality curve:

$$N^+/No = 1 - N/No = \left[ 1 - e^{-v \cdot D} \sum_{k=0}^{n-1} (v \cdot D)^k/k! \right]^m$$

and the extension corresponding to m targents of different volumes:

$$N^+/No = \prod_{i=1}^{m} (1 - Bi)$$

wherein $$Bi = e^{-v \cdot D} \sum_{k=0}^{n_i-1} (v \cdot D)^k/k!$$

From the above formulae, it is to be noted that, the greater the target and with the same dose mortality is higher, which leads to the assumption that viruses greater than Picornavirus will have lower inactivation doses.

In Table II other important formulae of the Target Theory are listed.

It is to be noted that doses in excess do no lead to the required result, in what concerns to vaccine preparation. In fact, the object is to destroy nucleic acids but not to affect proteins which give raise to the required antigenicity.

TABLE II

OUTSTANDING PARTICULAR RELATIONSHIPS OF THE TARGET THEORY

1. Survival curve for the case of: 1 impact - 1 target
   $N/No = e^{-v \cdot D}$
2. Survival curve for the case of: 1 impact - 1 target, two different sizes
   $N/No = a \cdot e^{-v1 \cdot D} + (1 - a) \cdot e^{-v2 \cdot D}$
3. Survival Curve TITRATION-DOSE
   $T = q \cdot D$
4. Survival line slope q.
5. Dose of 37% survival
   $D_{37} = - \log e/q$
6. Target molecular weight
   $MW_t = $ Avogadro No./$D_{37}$
7. Target sensitive volume
   $v = 1/D_{37}$ Low temperatures are used during the virus inactivation step, since they freeze water in the saline solution, avoid the higher activity of certain chemical species in a liquid medium, even with not in excess.

Figure 1:
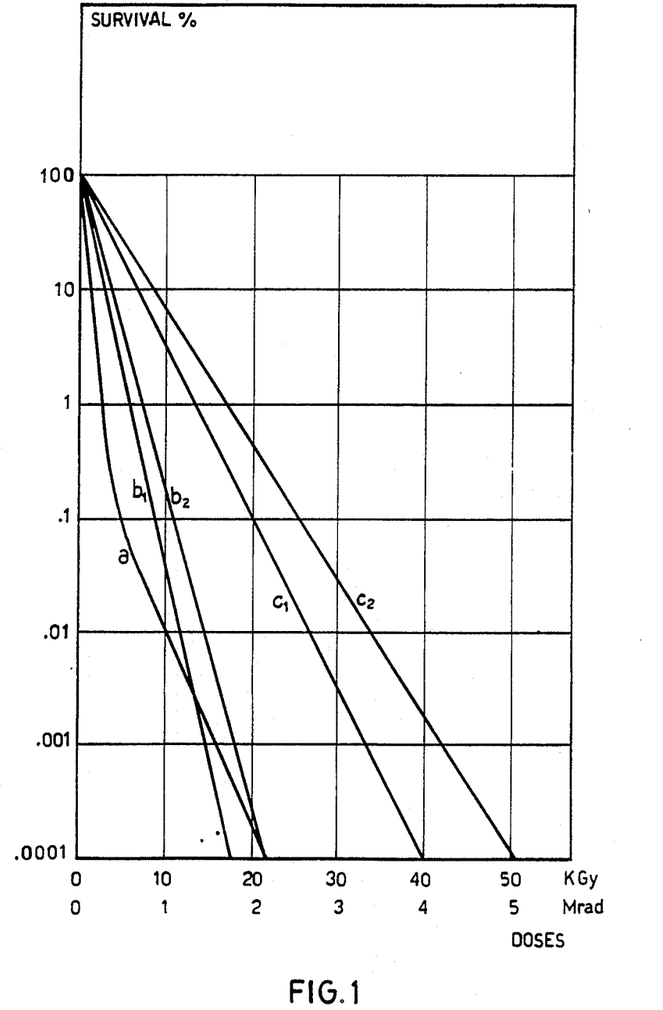
FIG. 1 is a graph plotting virus survival vs. radiation dose received.
Figure 2:
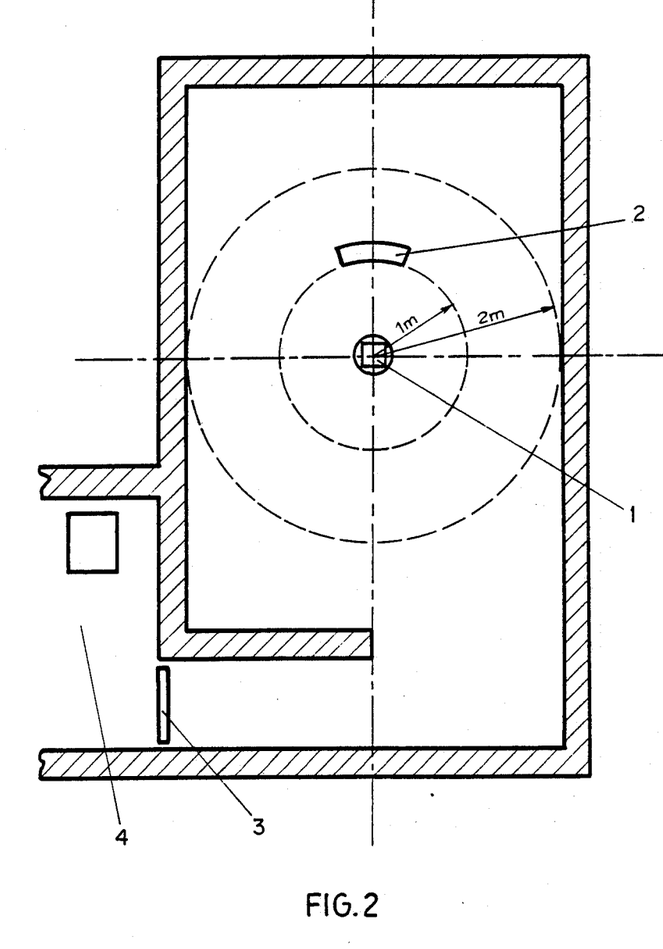
FIG. 2 is a scheme of the arrangement used for radiating ovine and bovine cattle.

As mentioned in connection with FIG. 1, three types of viruses have been tested, with different morphological features, thus embracing the whole spectrum of molecular weights and sizes, chemical composition and molecular structure.

Foot and mouth disease virus was obtained from large stocks of stains "A", "C" and "O" existing in Argentina.

Rauscher virus was received from Dr. Komitowsky from the Experimental Pathology Institute, German Cancer Investigation Center (DKFZ), Heidelberg, and was taken from original stocks from Bayer-Leverkussen laboratories.

Herpes Simplex virus was received from Dr. Darai, Medical Virology Institute, Heidelberg University; it corresponds to strains HSV-1 (Thea) and HSV-2 (Müller).

The last two viruses pertain to oncogenic virus families, Class C, with RNA genome (Rauscher) and DNA genome (Herpes Simplex).

The outstanding morphological features of the viruses usd in the tests are summarized in the following Table III.

TABLE III

| CHARACTERISTICS | | FOOT AND MOUTH DISEASE | RAUSCHER | HERPES |
| --- | --- | --- | --- | --- |
| Group | | Picornavirus | Retrovirus | Herpesvirus |
| Size (A) | | 250 | 800-1200 | 1800-2000 |
| Virions morphology a. coating | | bare | encapsulated | encapsulated |
| Virions morphology b. geometry | | icosahedron | helical | icosahedron |
| Capsomer No. | | 32 | none | 162 |
| Nucleic Acid | Molecular weight $\times 10^6$ d | 2,7 | 10 | 68 |
| | Chain framework | simple RNA | simple RNA | double DNA |

TABLE III-continued

| CHARACTERISTICS | FOOT AND MOUTH DISEASE | RAUSCHER | HERPES |
|---|---|---|---|
| Ploidism | haploid | diploid | conjugated |

FIG. 1 shows coincidence among the results obtained through theoretical provisions.

Survival curves based on experimentally determined doses correspond, in accordance with the target theory, to the following two main types:

(a) In what concerns to foot and mouth disease virus and herpes virus, the relationship found is purely exponential, therefore, its semilogarithmic representation vs. dose is a straight line. This is explained by the existence of a single target, destroyed with a single impact (a single sensitive volume), corresponding to expression 1 of Table II.

(b) Regarding Rauscher virus, straight line disruption is noted and the line adapts to the curve obtained in the model of 1 target and 1 impact, but of two different sizes. Expression 2 of Table II is applicable.

In all cases, value of 37% survival (D 37 dose) may be obtained through expressions 3, 4 and 5.

Upon knowing the above parameters, molecular weight MW and volume of the sensitive target may be calculated (Expressions 6 and 7).

Target size in expression 7 indicates that the mean impact value within the volume after dose D37 is 1.

The above is basically important since it means that the total impact number coincides with the number of radiated objects, thus allowing transference of the particular dose in erg/gram to impact No./gram, taking into account the first postulate of the target theory.

In order to compute the target volume or its molecular weight, the following equivalences were used:

(1) Average energy per impact E=60 (eV)
(2) Definition of $$1 \text{ rad} = 100 \text{ (erg)}/\rho = 6.24 \times 10^{13} \text{ (eV)}/\rho$$
$$= 6.24 \times 10^{13}/60 \text{ (impacts)}/\rho$$
$$= 1.04 \times 10^{12} \text{ (impacts)}/\rho$$

(3) Target volume $$v = 0.96 \times 10^{-12}/\rho \cdot D37 \text{ (cm)}$$

wherein $\rho$=density (g/cm$^3$) and D 37 in rads
(4) Target molecular weight $$MW_t = 5.8 \times 10^{11}/D37 \text{ (daltons)}$$

wherein D 37 is in rads

FIG. 3 depicts some of the most important structural components of viruses under study, related to the instant invention.

Figure 3A:
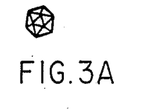
FIG. 3 shows some of the most important components of the viruses under study.
Figure 3B:
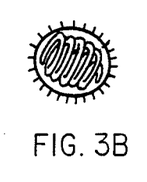
Figure 3C:
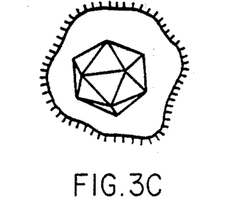

Relative sizes of the viruses may be seen in -A-, -B- and -C-. In a scale in which the written width of a sheet corresponds to 1 micrometer:
-A-: foot and mouth disease virus
-B-: Rauscher Leukemia virus
-C-: Herpes virus -A- represents a polyhedral structure and cubic symmetry virus. Among others, poliomyelitis virus is included in this group. -B- and -C- represent viruses bearing a more complex symmetry. Both are encapsulated, but interal components have different structures: one is helical and the other is cubic, such as is the case with foot and mouth disease virus.

Figure 3D:
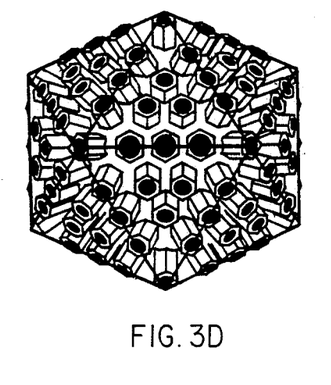

In -D- the nuclear is represented in a larger scale, and corresponds to that of 162 capsomers Herpes virus. Pentamers may be seen at the corners and hexamer capsomers in the remaining sites.

Figure 3E:
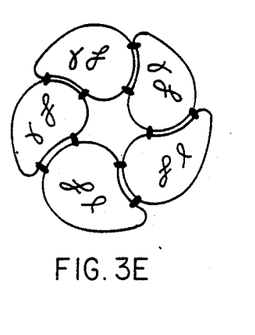
Figure 3F:
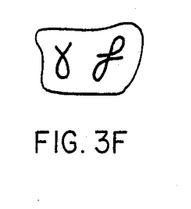

-E- shows, in a larger scale, details of the formation of a pentamer from more elemental structural units, such as that shown in -F-.

These units, formed by one or more polypeptides, similar or not, constitute the antigen monomers the properties of which should be preserved in the viral inactivation step. These chains are proteins which, in many cases, were able to isolate and correspond to units such as VPI of foot and mouth disease, or such as P 18 and P24 of AIDS virus, and which have a molecular weight not higher than 24.000 daltons. On the other hand, this value corresponds to that generally assigned as maximum value to a structural protein with antigenic properties.

Figure 4:
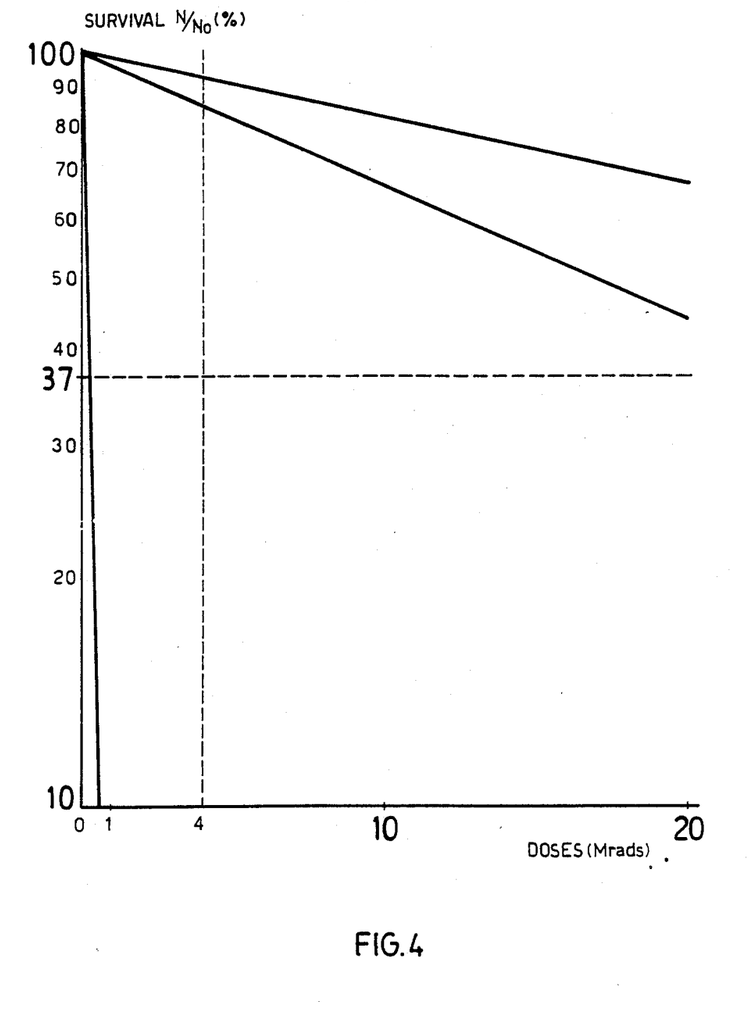
FIG. 4 is a survival semilogarithmic curve, in accordance with the Target Theory, for different sizes of targets.

FIG. 4 is a graph listing the outstanding results permitting the creation of a methodology useful for the preparation of viral vaccines through nucleus radiation inactivation, preserving the antigenic ability given by smaller size units.

Curve (A) represents survival of a protein with an average molecular weight of 12.000 daltons vs. gamma radiation dose. Curve (B) represents survival of a protein with an average molecular weight of 24,000 daltons, under the same conditions.

These curves were obtained using the expressions deducted through the target theory.

Although curve (B) corresponds to the dimmensions of the antigen commonly found in some viruses, such as that of foot and mouth disease, this means an extreme value of dimmensions representing a viral antigen, since these molecules are sometimes cleaved into two or more equal components such as that shown with -F- in FIG. 3, or most important, the target volume sensitive to its antigenic properties represents a considerable smaller fraction than its total weight. Therefore, curve (A) is considered the most representative of structural viral antigen group.

Percentage values of antigens affected by radiation doses equivalents to those of viral inactivation (4 Mrads), vertical dotted line in figure 4, are 8% for the most probable curve (A), and 16% for curve (B) (damage limit) of 24,000 daltons. Further, this curve.corresponds to an extreme damage value produced by radiations, not only for viral antigens, but for the whole particle of the same molecular weight treated by radiations under identical experimental conditions, such as those indicated when disclosing the target theory.

Curve (C) of $2.7 \times 10^6$ daltons expresses inactivation of foot and mouth disease virus through gamma radiation. As seen in FIG. 1, this is the radio-sensitive extreme value for viruses under study. This is in fact due to the corresponding with infective nucleus of single chain to ribonucleic acid, under the most radioresistant conditions.

The same above reasons are the grounds for assuming that not only these viruses under study, corresponding to a wide spectrum of morphological and structural features, will have a limit behaviour expressed by curve (C), but also most of the viruses will have the same behaviour when exposed to electromagnetic radiation doses, i.e. will be at the left of curve (C). This is due to the fact that the existence of viruses with molecular weights notably lower than those corresponding to picornavirus has not been demonstrated and, further, since viruses with higher molecular weights have been found just between curve (C) and the Y-axis.

Viral inactivation carried out with corpuscular radiations on the three viruses under study allows determining their lower efficiency in the same doses.

Foot and mouth disease virus was inactivated with 27 MeV deuterons, thus demonstrating a biological efficiency of 0.7, which would indicate the need of applying a higher dose than that used in the case of electromagnetic radiations, for the same inactivation value. This result is respresented by curve -c2- of FIG. 1.

The other two virus irradiated with other particles: 10 MeV electrons, 104 MeV alpha particles and 52 MeV deuterons gave a similar result, thus indicating a relative biological efficiency lower than 1, as in the case of foot and mouth disease.

We claim:

1. A process for preparing an antiviral viccine, paticularly anti-foot and mouth disease vaccine, which process comprises the steps of:
   (a) radiating an animal free of active virus with ionizing radiations;
   (b) innoculating active virus into said animal;
   (c) maintaining the animal under controlled sterile conditions and under antibiotic administration until a high viral proliferation is obtained;
   (d) after animal's death, cooling the cadaver;
   (e) withdrawing skin and viscerae from the animal cadaver;
   (f) crushing the soft portions of the remaining parts of the cadaver with the aid of a saline solution in order to obtain a visually homogeneous mixture;
   (g) mechanically separating an active viral suspension from said mixture;
   (h) transforming the active viral suspension into an inactive viral suspension through the application of ionizing radiation on said suspensions, which are maintained at a temperature substantially lower than 0° C.; and
   (i) formulating the vaccine from said inactive viral suspension.

2. A process as claimed in claim 1, wherein a period of substantially 24-36 hours elapses between animal radiation and active virus animal inoculation.

3. A process as claimed in claim 1, wherein:
   (a) the active virus used in animal inoculation is an injectable suspension of active foot and mouth disease virus;
   (b) an anti-foot and mouth disease vaccine is formulated in the formluating step.

4. A process as claimed in claim 3, wherein the ionizing radiation dose of the animal radiating step is substantially comprises between 700 and 2,700 rads.

5. A process as claimed in claim 3, wherein the dose applied when transforming the active viral suspension into an inactive viral suspension is substantially of 2-6 Mrad, said suspensions being maintained at temperatures substantially lower than 0° C.

6. A process as claimed in claim 4, wherein said animal is an adult rodent.

7. A process as claimed in claim 4, wherein said animal is a ruminant.

8. A process as claimed in claim 1, wherein the mechanical method employed when separating the active viral suspension from the visually homogeneous mixture consists in the filtration of said mixture.

9. A process as claimed in claim 1, wherein the mechanical method used when separating the active viral suspension from the visually homogeneous mixture consists in the centrifugation of said mixture.

10. A process as claimed in claim 3, wherein the vaccine formulating step comprises:
    (a) placing the inactivated viral suspension into a first tank at 4° C.;
    (b) mixing a mineral oil with sorbitan sesquioleate HLB 3.7 as lipophilic emulgent; with polyoxiethylene sorbitan mono-oleate HLB 15 as hydrophilic emulgent, and with n-butanol as co-surfactant, in a second tank at 4° C.;
    (c) pouring the contents of the first and second tanks into a homogenizator;
    (d) homogenizing, under high pressure, at 4° C., and under continuous flow, in sterile closed loop, until a stable emulsion, of the "water in oil" type, having homogeneous droplets of no more than 0.1 micron in diameter is obtained;
    (e) collecting the emulsion into a third tank, thus obtaining the vaccine so prepared.

11. A process as claimed in claim 10, wherein:
    (a) when placing said inactive viral suspension into a first tank, the suspension is mixed with aluminum hydroxide, stirred for 2 hours and settled for 24 hrs, then the supernatant is removed until the original volume of aluminum hydroxide is attained;
    (b) when mixing a mineral oil with emulgents, said mineral oil is mixed with sorgitan sesquioleate HLB 3.7 as lipophilic emulgent, polyoxiethylene sorbitan mono-oleate HLB 10 as hydrophilic emulgent and n-butanol as co-surfactant.

12. A process as claimed in claim 11, wherein said mineral oil is liquid paraffin without cyclic hydrocarbons.

13. A process as claimed in claim 11, wherein said mineral oil is polybutene.

14. A process as claimed in claim 3, wherein the ionizing radiations used for radiating said animal are electromagnetic radiations.

15. A process as claimed in claim 3, wherein the ionizing radiations used for radiating said animal are particle radiations.

16. A process as claimed in claim 3, wherein the ionizing radiations used in transforming the active viral suspension into an inactive viral suspension are electromagnetic radiations.

17. A process as claimed in claims 3, wherein the ionizing radiations used in transforming the active viral suspension into an inactive viral suspension are particle radiations.

* * * * *